Figure 3:
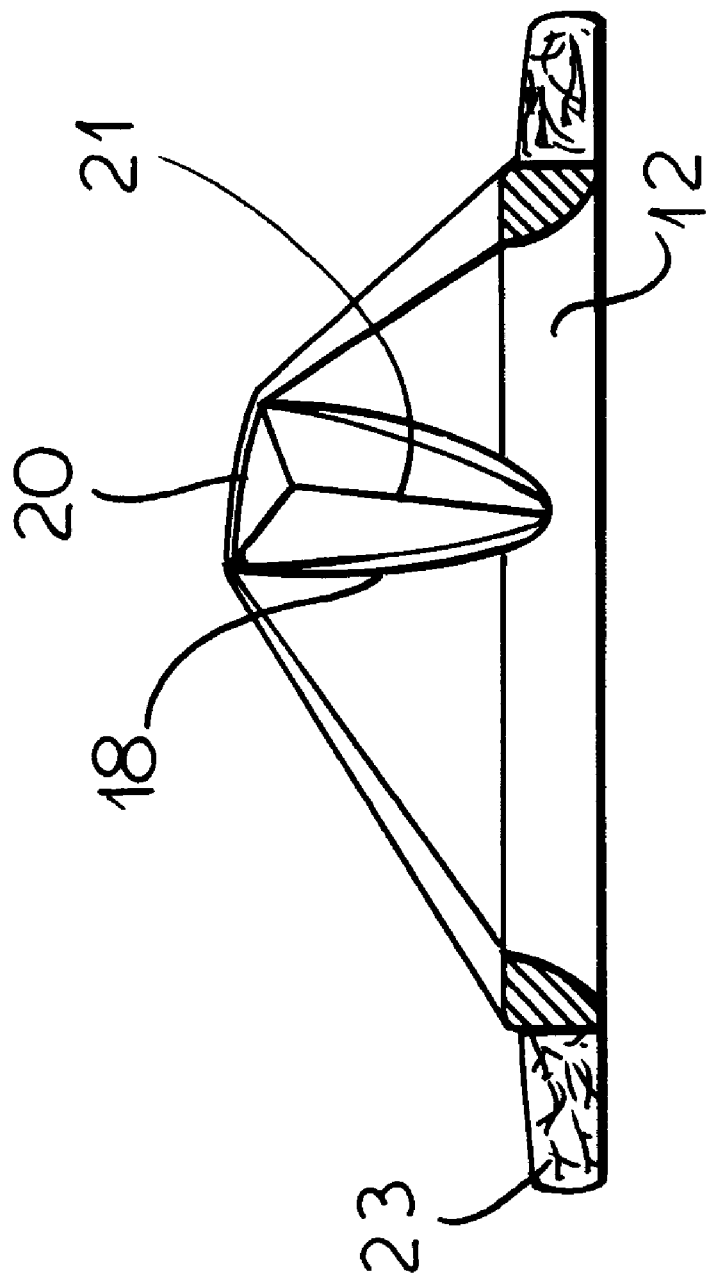

United States Patent
Jansen

[11] Patent Number: 6,086,612
[45] Date of Patent: Jul. 11, 2000

[54] MITRAL VALVE PROSTHESIS

[75] Inventor: Josef Jansen, Köln, Germany

[73] Assignee: Adiam Medizintechnik GmbH & Co. KG, Erkelenz, Germany

[21] Appl. No.: 09/194,045

[22] PCT Filed: Jun. 18, 1997

[86] PCT No.: PCT/DE97/01297

§ 371 Date: Nov. 17, 1998

§ 102(e) Date: Nov. 17, 1998

[87] PCT Pub. No.: WO97/49355

PCT Pub. Date: Dec. 31, 1997

[30] Foreign Application Priority Data

Jun. 24, 1996 [DE] Germany ............ 196 25 202

[51] Int. Cl.[7] .................................................. A61F 2/24
[52] U.S. Cl. .................................. 623/2.17; 623/2.18
[58] Field of Search ............................. 623/2.1, 2.11, 623/2.2, 2.21–2.29, 2.3, 2.23, 2.31–2.35, 2.14, 2.17, 2.18, 900

[56] References Cited

U.S. PATENT DOCUMENTS

| | | | |
|---|---|---|---|
| 4,204,283 | 5/1980 | Bellhouse et al. ............... | 623/2.1 |
| 4,218,783 | 8/1980 | Reul et al. . | |
| 4,225,980 | 10/1980 | Ramos Martinez ............ | 623/2.1 |
| 4,306,319 | 12/1981 | Kaster ........................... | 623/2.1 |
| 4,340,977 | 7/1982 | Brownlee et al. . | |
| 4,491,986 | 1/1985 | Gabbay . | |
| 4,759,759 | 7/1988 | Walker et al. . | |
| 5,156,621 | 10/1992 | Navia et al. . | |
| 5,197,980 | 3/1993 | Gorshkov et al. ............... | 623/2.1 |
| 5,908,452 | 6/1999 | Bokros et al. ................... | 623/2.1 |
| 5,951,600 | 9/1999 | Lemelson ....................... | 623/2.1 |
| 6,007,577 | 12/1999 | Vanney et al. .................. | 623/2.1 |

FOREIGN PATENT DOCUMENTS

| | | |
|---|---|---|
| 0 183 904 | 6/1985 | European Pat. Off. . |
| 2 548 888 | 1/1985 | France . |
| 42 22 610 A1 | 1/1994 | Germany . |
| WO 91/19465 | 12/1991 | WIPO . |

*Primary Examiner*—David H. Willse
*Assistant Examiner*—Suzette J. Jackson
*Attorney, Agent, or Firm*—Herbert Dubno

[57] ABSTRACT

A mitral valve prosthesis consists of a support housing with a large base ring that bears two stays which substantially extend in the ring axis direction and are connected by curved walls for securing two flexible cusps. The free ends of the stays form an inner support for the cusps. In order to avoid a possible mutual interference between the heart and valve functions, the base-ring (12) has in the top view a closed, non-round shape with a common longitudinal axis (15) but two transverse half-axis (16, 17) of different sizes. The stays (18, 19) lie on the longitudinal axis (15) and form the transition between the two halves of the valve. The less curved wall (13) carries a mural cusp (11) having a smaller surface and a higher angle of inclination relative to the base ring base surface than the more curved wall (14).

13 Claims, 3 Drawing Sheets

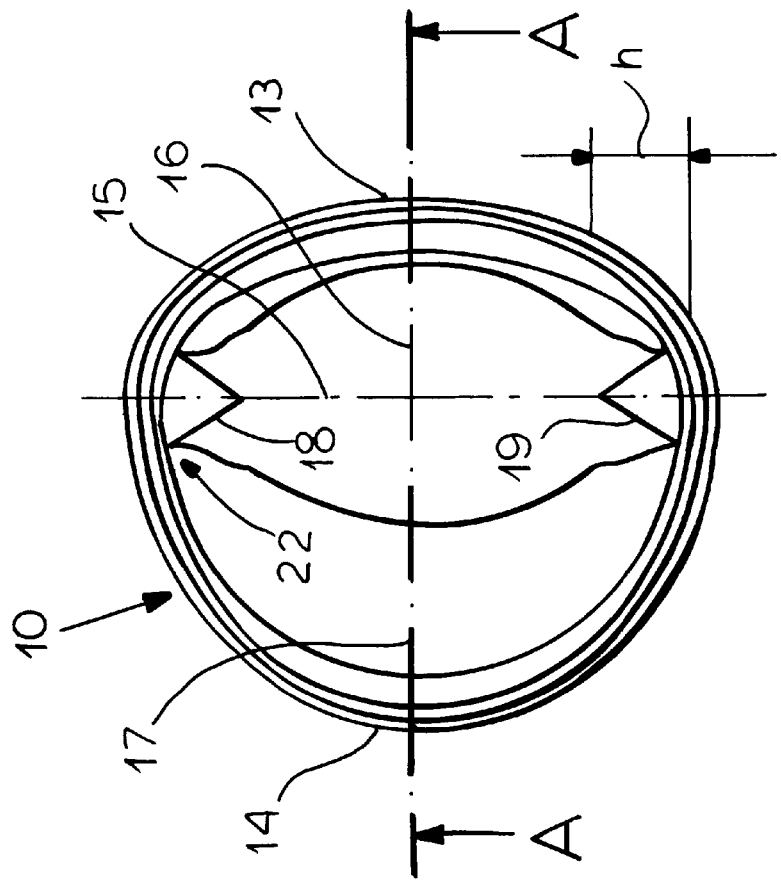
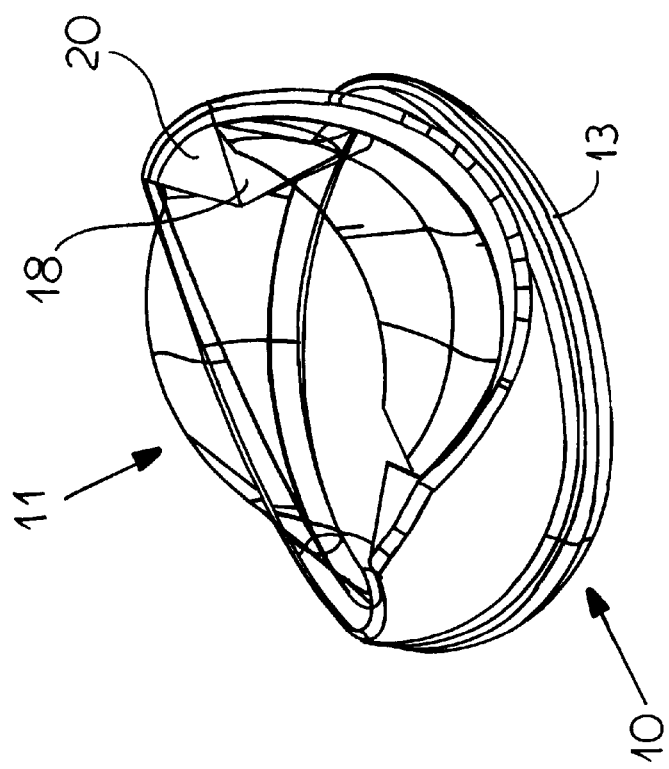
FIG.2
FIG.1

MITRAL VALVE PROSTHESIS

The invention relates to a prosthetic mitral heart valve comprised of a support housing (stent) with a base ring carrying two posts extending substantially in the axial direction of the ring via arcuate walls which serve to affix two flexible cusps [leaflets] and whose free ends form an inward abutment for the cusps [leaflets].

Such mitral heart valves are sutured by means of a suture ring fastened on the base ring in the body tissue.

The first mitral heart valves known from the state of the art had a circular tubular valve housing in which the two cusps [leaflets] were arranged and which had configurations corresponding to shapes cut from a cylindrical surface and which in the closed state braced against one another and in the open state lay against the cylinder wall of the valve housing. As has already been indicated in DE 27 42 681 B2, the closing characteristics of such heart valves were not optimal. Furthermore, a relatively long valve housing was required. To provide assistance as to this point, it was proposed in the aforementioned publication, instead of two cusps [leaflets] to utilize only a single membrane which corresponded to a part of the surface of an elliptical cylinder and which was cut from a circular cylinder. The valve housing was then an elliptical cylinder formed form a circular tube cut at an angle of 90°, whereby the membrane was affixed along half the periphery of this cut edge between its two extremal points which corresponded to the posts mentioned at the outset. In this embodiment which eliminated the need for two cusps [leaflets], a folding of cusps [leaflets] in their closed condition as they lay against one another was eliminated but one could not prevent an unsatisfactory valve closure.

In prosthetic heart valves the varying physiological loading conditions arose in the form of different closing pressure differentials to which the heart valve must be matched which thereby posed a further problem. With such closing pressure differentials, radial force components are applied by the cusps [leaflets] to the posts mentioned at the outset and which deform radially inwardly toward the center of the valve. With increasing closing pressure differentials, the cusps [leaflets] can cave in and thus bulge inwardly so that they lie against one another with practically complete overlapping of the cusps [leaflets] and thus a desirable sealing of the valve, although with higher pressure differentials, the overlapping can be excessive at the free cusp [leaflet] edges and that can give rise to undesired folding of the cusps [leaflets]. To reduce the high stresses in the upper cusp [leaflet] regions which correspond to the boundaries at the stent peaks and the natural commissures, it has already been proposed to construct the posts so that they will be flexible in their upper portions. This can, however, lead to undesirable creeping effects and hence premature material fatigue. In order to limit deformation of the posts radially inwardly toward the valve axis, it has thus been proposed in DE 42 22 610 A1 to make the free post ends rigid, especially by an accumulation of material in the form of a prismatic inner layer in the free post ends which in cross section is triangular. The prismatic inner layer should taper in a concave manner toward the stent base, i.e. toward the inlet region of the heart valve.

It is the object of the present invention to improve the mitral heart valve described at the outset by imparting to it a new shape and a new structural configuration so that a potential countervailing functional detriment to the heart and the valve will be avoided. This object is achieved with the prosthetic mitral heart valve according to claim 1 which is characterized in accordance with the invention in that the base ring—considered in plan view—has a closed nonround shape with a common longitudinal axis, but two half transverse axes of unequal size, whereby the posts lie along the longitudinal axis and form the transition regions from one to the other half shape and whereby the wall with reduced curvature carries the smaller area (mural) cusp [leaflet] at a more steeply inclined angle to the base ring ground surface than the wall with the larger curvature. The two semishapes thus form a stent body which largely approximates the natural mitral valve of a heart which has a D shape or kidney shape. To the extent that, for example, in U.S. Pat. No. 5,415,667 so-called biological mitral valves without stents are described, these have, by contrast to the mitral heart valves of the invention, the distinction that the aortal cusp [leaflet] is arranged at the side with reduced curvature while the mural cusp [leaflet] lies in the region which has the greatest curvature. The semi-forms can be semiellipses, hyperbolas or other shapes in which the boundary conditions ensure that the transition points of both halves continuously are differentiable.

Preferably the cusp [leaflet] inclinations which are determined by the orientation of the connecting lines of the cusps [leaflets] with the upper inner edges of the walls lie between 25° and 45° for the less inclined (aortal) cusp [leaflet] and between 40° and 65° for the more strongly inclined (mural), each relative to the base surface. The more strongly inclined cusp [leaflet] has at least a 5° greater angular setting than the cusp [leaflet] of lesser inclination.

According to a further feature of the invention, the main flow direction is inclined by about 10° to 25° preferably by about 15° from the normal to the mural cusp [leaflet]. Because of this feature the risk of interference and possible distortion of the support housing and the juxtaposed heart chamber inner walls is reduced. The cusps [leaflets] form a distinctive funnel-shaped opening passage with a reduced cross section by comparison to the aorta valve. The described arrangement and configuration ensures an efficient physiological flow path from the atria into the ventricles. The illustrated heart valve according to the invention can be fabricated with a reduced height than configurations known in the art. This is true especially as to the circular cross sectional shape or the symmetrical elliptical support housing.

In a preferred embodiment, the lengths of the half transverse axes of the semiellipses of the support housing are in a ratio of 1.5 to 2.5:1. Especially with a semi-axis ratio of 2:1 is the shape close to that of natural mitral valve. The common longitudinal axis of the two different semiellipses of the support housing with a length between 10 mm and 45 mm.

Preferably the posts are integrated into the walls with the same thickness as that of the walls, i.e. the described posts do not project any longer from the wall regions but rather the wall in the region of the posts extends upwardly out of the wall, preferably to a point or a flattened post end.

As has been described already in principle in DE 42 22 610 A1, the posts can, as an alternative to the aforedescribed embodiment, be configured to be prismatic. The posts tend to become thicker toward their free ends to the aforementioned end face dimensions, preferably continuously. Conversely, the posts narrow toward the base ground surface substantially conically where they end in the inlet region, i.e. ahead of the lower edges of the base ring by transitions into the base ring wall thickness there.

In order to prevent the valve cusps [leaflets] from being strongly stressed in the commissure regions, according to a further feature of the invention the connecting line of the cusp [leaflet] with the upper inner edge of the wall on each side is caused to lie in a plane. With this configuration of the wall end surface with the cusp [leaflet] attachment takes place, high stresses are avoided.

If the posts of the support bodies are so arranged that their longitudinal axes are inclined to the main flow direction relative to the base surface, i.e. by 0° to 20°, the mitral heart valve from the viewpoint of flow cross section, structural height and its stability is further improved. With the described mitral heart valve, many of the structural and material-based risks of embodiments known from the state of the art can be avoided. With the construction according to the invention of the mitral heart valve, there is a further approximation of the shape of the natural mitral valve. By contrast with the bioprosthesis as mitral valve replacements, which in 50% of the cases require administration of anticoagulant medication, the mitral valve prosthesis of the invention can function medication-free, since the flow guidance through the combination of the cusp [leaflet] openings and the flow cross section of the valve tends to largely minimize mechanical damage to the blood.

Figure 4:
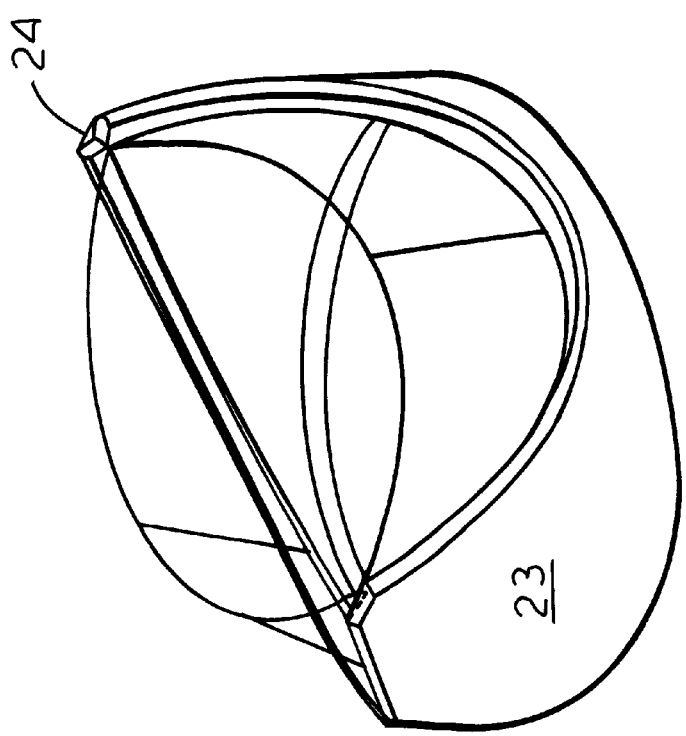

An embodiment of the invention is illustrated in the drawing. I shown:

FIG. 1 a perspective view of a prosthetic mitral heart valve,

FIG. 2 a plan view of the heart valve according to FIG. 1,

FIG. 3 a section along the line A—A,

FIG. 4 a perspective view of a further prosthetic mitral heart valve, and

Figure 5:
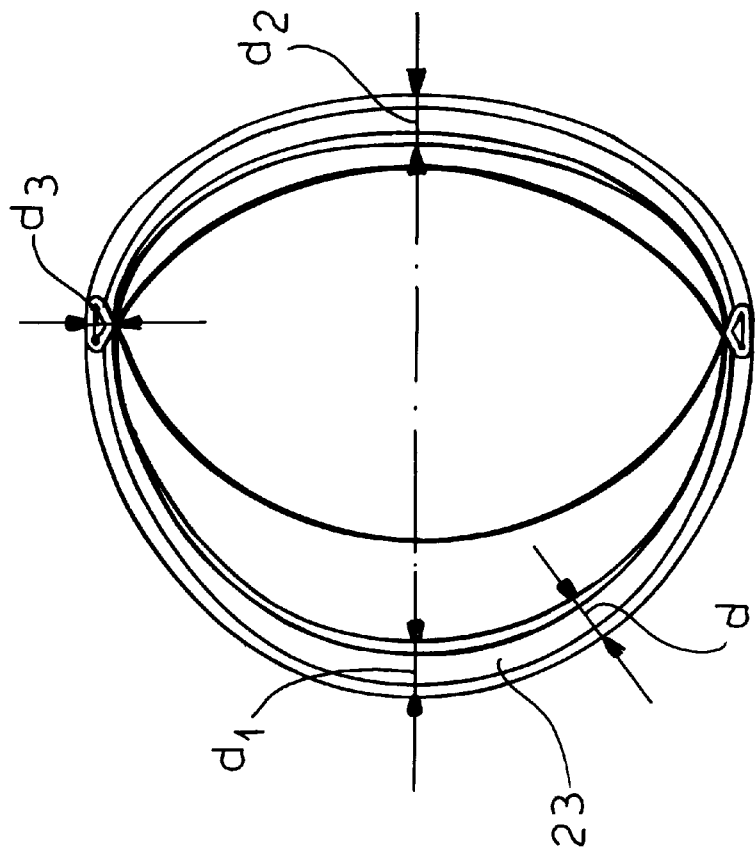

FIG. 5 a plan view of the heart valve according to FIG. 4.

The prosthetic mitral heart valve is comprised of a support housing 10 with two cusps [leaflets] 11. The support housing 10 is sutured in the valve annulus of the patient tissue by means of a suture ring 23. The support ring is comprised of a thermoplast like polyamide, which is manufactured to a limitedly bending elastic body and then provided with an outer coating of polyurethane. The one-piece support housing 10 has a base ring 12 whose inner edges are rounded outwardly in a manner known from the state of the art. For better attachment of the suture ring 23, the base ring on the outer wall can have a bulge. The wall substantially perpendicular to the base ring ground surface is subdivided into a first wall portion 13 with reduced curvature and a second wall portion 14 with the greater curvature that together form, in a plan view of the base ground surface, two imaginary half shapes with a common longitudinal axis in plan view. Accordingly the half transverse axes 16 and 17 can be of different lengths, preferably amounting to a length ratio of 1:2. Up to approximately a bulge in the base ring region, the outer wall of the wall portions 13 and 14 is curved but smooth. Correspondingly the same applies to the inner wall of the wall portions 13 and 14 except for the posts 18, 19 which are yet to be described. The wall thicknesses of the wall portions 13 and 14 are different and the wall thickness becomes minimum toward the post regions or is the greatest at the middle region; preferably the wall thickness in the middle regions between the posts is twice as great than in the regions close to the post.

The upper end faces of the walls 13 and 14, to which the cusps [leaflets] are attached, is inclined toward the exterior and lies substantially up to the region of the posts in the form of an intersection which is given by a cut of the respective half shape with an inclined plane inclined thereto. For the adhesive attachment of prefabricated cusps [leaflets], the bonding line of the cusp [leaflet] with the upper inner edge of the wall portions 13 and 14 lies in a plane which forms an angle of about 56° for the upper edge of the wall 13 or of about 41.54° for the upper edge of the wall 14 relative to the base ring ground surface. The end faces can also run tangential to the planes which the respective cusps [leaflets] assume in the closed state. The arrangement of the upper inner edges of the wall portions 13 and 14 in planes which are inclined in respective angles, has the advantage that both cusps [leaflets] can be cut from flat synthetic resin foil and without tensile stresses or without the danger of fold formation and can be cemented to the upper edges of the walls up to the regions close to the posts.

The material for the cusps [leaflets] can be synthetic resin foils known from the state of the art, preferably thermoplastic elastomers or synthetic resins with elastomeric properties, preferably the cusps [leaflets] are comprised of flexible polyurethane foil.

The posts 18 and 19 widen toward their upper end faces 20 uniformly. In a plan view upon the inner support ring 10, the posts appear to be V shaped and end wedge-like above the base ring ground surface at the inlet region of the support housing 10. The post longitudinal axes 21 are not perpendicular to the base ring ground surfaces but rather are slightly inclined with respect to surface normals, for example at an angel of 65°. The corresponding inclination of about 15° characterizes also the end face 20 of the posts relative to the base ring ground surface. The posts 18, 19 or their end faces 20 replace the commissure cusps [leaflets] of the natural valve and serve with their approximately equal length triangle shanks as inner seats for the cusps [leaflets] 11.

In the transition region 22 between the equilength triangle shanks and the wall portions 13 and 14, the support housing is configured as rounded. The cusps [leaflets] 11 are adhesively bonded to the upper edges of the wall portions 13 and 14 with the support housing and are so cut that in the closed state they rest laterally isosceles post edges and between the posts rest linearly on the opposing cusp [leaflet]. The commissure region formed by the posts 18 and 19 prevent the penetration of the cusps [leaflets] past the post [inversion] and thus serve together with the overlapping region along the longitudinal axis 15 of the cusps [leaflets] 11 as a cusp [leaflet] bracing. The connection lines of the cusps [leaflets] 11 with the wall portions 13 and 14 which lie in a plane up to the commissure regions, ensures a uniform force distribution between the cusps [leaflets] 11 and the support housing, thereby especially avoiding high radial tensile stresses on the post ends or in the regions adjoining the posts as have required in the known constructions in the state of the art, material accumulations in the support housing which gave rise to the so-called creeping.

The configuration of the support housing 10 is largely matched to the natural D shape or kidney shape, whereby the mural cusp [leaflet] at the upper edge of the wall portion 13 has a steeper setting angle and the aortal cusp [leaflet] at a wall portion 14 has a shallower setting. This results in a reduced structural height of the mitral heart valve whose main flow direction is not coaxial but is inclined by about 15° thereto.

FIG. 4 shows an alternative embodiment of a mitral heart valve in which the aforedescribed posts are not bodily visible. Rather in this embodiment the posts are of the same thickness as the wall portions and are integrated in the wall 23. The wall portions at opposite ends extend upwardly to a post end 24 with a point or, as shown, a flat.

The thickness of the wall portions d can decrease from the base ring to the upper edge of the wall portion continuously. As can be seen better from FIG. 5, the thickness d of the wall portion 23, measured at the level of the base ring, is a minimum at the posts and increases to a maximum value. In a concrete embodiment the thickness $d_1$ amounts to 2.57 mm, the thickness $d_2$ amounts to 2.34 mm and the thickness $d_3$ (in the region of both posts) amounts to 1.4 mm.

In the production of the described heart valves, the respective finished cusps [leaflets] can be cemented or welded onto the end faces of the support housing. Alternatively it is also possible to manufacture the heart valve by means of the injection molding technique known in the state of the art, including the two-component injection in which initially the support housing is made and then the cusps [leaflets] are applied by injection molding. A further possibility is the use of the so-called immersion technique. For this purpose a support housing which is made from polyamide, feature a coating with polyurethane, is shoved onto a corresponding immersion mandrel with shaping surfaces for the cusps [leaflets] and the immersion mandrel with the support housing is then immersed in a liquid synthetic resin solution (polyurethane) and moved with a tumbling movement therein until the desired thickness distribution is reached. During the tumbling the synthetic resin hardens.

The invention extends also to artificial blood pumps (artificial hearts), conduit valve implants, bioprostheses or mechanical prostheses and the like in which the support housing is an integrated component of a tubular housing or hose.

What is claimed is:

1. A prosthetic mitral heart valve comprised of a support housing (20) with a base ring (12) which carries two posts (18, 19) extending in the axial direction of the ring and separated by arcuate wall portions (13, 14) to which the posts are connected and which serve for affixing two flexible cusps or leaflets (13, 14) to which the posts are connected and which serve for affixing two flexible cusps or leaflets (11), the posts having free ends forming inner seats for the cusps or leaflets (11) characterized in that the base ring (12) seen in plan view, has a closed nonround configuration with a common longitudinal axis (15) but two half transverse axes of unequal length (16, 17), whereby the posts (18, 19) lie on a longitudinal axis (15) and form the transition regions from one of the other half shapes, whereby the wall portion with the smaller curvature carries the smaller area mural cusp leaflet with the steeper angle than the wall portion (14) with larger curvature.

2. A prosthetic mitral heart valve according to claim 1, characterized in that the cusp leaflet inclination which is determined by the position of the connection line of the cusp leaflet (11) with the upper inner edge of the wall portion (13, 14) lies between 25° and 45° for the less inclined aortal cusp leaflet and between 40° and 65° for the more strongly inclined mural cusp or leaflet, each with respect to the base ground surface, and simultaneously the more strongly inclined cusp or leaflet is inclined at an angle of at least 5° more than the lesser inclined cusp or leaflet.

3. A prosthetic mitral heart valve according to one of claims 1 or 2, characterized in that the main flow direction is inclined by about 10° to 25°, preferably about 15° from the normal to the mural cusp or leaflet.

4. A prosthetic mitral heart valve according to one of claims 1 to 3, characterized in that lengths of the half transverse axes (16, 17) is in a ratio of 1.5 to 2.5:1.

5. A prosthetic mitral heart valve according to one of claims 1 to 4, characterized in that the common longitudinal axis (15) has a length between 10 mm and 45 mm.

6. A prosthetic mitral heart valve according to one of claims 1 to 5, characterized in that the posts are integrated to be equal in thickness of the wall (23).

7. A prosthetic mitral heart valve according to claim 6, characterized in that the end faces of the posts ends (24) are pointed or flattened.

8. A prosthetic mitral heart valve according to one of claims 1 to 7, characterized in that the wall thickness D of the base ring decreases toward the upper edge of the wall portions, preferably continuously.

9. A prosthetic mitral heart valve according to one of claims 1 to 5, characterized in that the posts (18, 19) increases in thickness toward their free ends to the end face dimensions, preferably continuously.

10. A prosthetic mitral heart valve according to claim 9, characterized in that the posts (18, 19) converge wedge-shaped toward the base ground surface and end before the inlet region.

11. A prosthetic mitral heart valve according to one of claims 1 to 10, characterized in that the thicknesses of the wall portions (13, 14) of the base ring (12) in the region between the posts (18, 19) i.e. at the cusp or leaflet bases, is greater than in the regions close to the posts, preferably by a factor of 1.4 to 2.3.

12. A prosthetic mitral heart valve according to one of claims 1 to 11, characterized in that the connection line of the cusps or leaflets of the upper inner edge of the wall portions (13, 14) each respectively lie in a plane.

13. A prosthetic mitral heart valve according to one of claims 3 to 12, characterized in that the post longitudinal axes (21) runs approximately in the direction of the main flow direction.

* * * * *